(12) United States Patent
Veale

(10) Patent No.: US 6,639,678 B1
(45) Date of Patent: Oct. 28, 2003

(54) APPARATUS AND METHOD FOR NONDESTRUCTIVE MONITORING OF GASES IN SEALED CONTAINERS

(75) Inventor: James R. Veale, Charlottesville, VA (US)

(73) Assignee: Lighthouse Instruments LLC, Charlottesville, VA (US)

( * ) Notice: Subject to any disclaimer, the term of this patent is extended or adjusted under 35 U.S.C. 154(b) by 102 days.

(21) Appl. No.: 09/615,739

(22) Filed: Jul. 13, 2000

(51) Int. Cl.$^7$ ............................................... G01N 21/61
(52) U.S. Cl. ........................................ 356/437; 356/440
(58) Field of Search ................................. 356/437, 438, 356/439, 440

(56) References Cited

U.S. PATENT DOCUMENTS

| | | | |
|---|---|---|---|
| 4,684,258 A | | 8/1987 | Webster |
| 4,934,816 A | | 6/1990 | Silver et al. |
| 5,048,958 A | * | 9/1991 | Conforti et al. ............ 356/440 |
| 5,155,019 A | * | 10/1992 | Sussman et al. ............ 356/437 |
| 5,267,019 A | | 11/1993 | Whittaker et al. |
| 5,317,156 A | | 5/1994 | Cooper et al. |
| 5,473,161 A | | 12/1995 | Nix et al. |
| 5,482,842 A | * | 1/1996 | Berndt ......................... 435/34 |
| 5,637,872 A | | 6/1997 | Tulip |
| 5,900,378 A | | 5/1999 | Mayer et al. |
| 6,014,256 A | | 1/2000 | Cheng |
| 6,134,000 A | * | 10/2000 | Schmid et al. ............... 356/440 |

OTHER PUBLICATIONS

Christopher R. Webster, *Brewster–Plate Spoiler: a Novel Method for Reducing the Amplitude of Interference Fringes that Limit Tunable Laser Absorption Sensitivities*, J. Opt. Soc. Am. B., vol. 2 No. 9, Sep. 1985, pp 1464–1470.

Joel Silver and Alan Stanton, *Optical Interference Fringes in Laser Absorption Experiments*, Appl. Opt. 27, 1914 (1988), 1914–1916.

David E. Cooper and Ramon U. Martinelli, *Near–infrared diode lasers monitor molecular species*, Laser Focus World, Nov. 1992, pp. 133–146.

James R. Veale, White Paper: *Tunable Diode Laser Absorption Spectroscopy (TDLAS): An Application to Oxygen Headspace Gas Analysis*, pp. 1–16, distributed Sep. 1998.

A printout (labeled W–1) of a Web site article by D.J.Brassington entitled, *Tunable diode laser absorption spectroscopy for the measurement of atmospheric species*, from the Atmospheric Chemistry Research Unit of the Imperial College of Science Technology and Medicine, identified as published in 1995, pp. 1–65.

A printout (labeled W–2) of a Web site article entitled "Diode Laser Gas Sensing,"4 pp., printed Jun. 28, 2000.

A printout (labeled W–3) of a chapter of a Web site article entitled "Tunable Diode Laser Absorption Spectroscopy,"6 pp., printed Jun. 28, 2000.

A printout (labeled W–4) of a chapter of a Web site article entitled "Theory of Fourier Transform Spectroscopy,"6 pp., printed Jun. 28, 2000.

* cited by examiner

Primary Examiner—Richard A. Rosenberger
(74) Attorney, Agent, or Firm—Greenblum & Bernstein, P.L.C.

(57) ABSTRACT

A system and method for nondestructive detection of gas in a sealed container. The system includes a tunable diode laser source that provides a uncollimated laser beam for absorption in a substance to be measured, a detector that detects the laser beam, and a zone that accepts one or more of the selected containers. Each container is substantially optically transparent and may contain the substance to be measured. The zone is located between the detector and a laser source configured to transmit the laser beam through the zone. The invention also includes a collection lens that focuses the laser beam onto the detector, the collection lens being located between the zone and the detector.

23 Claims, 6 Drawing Sheets

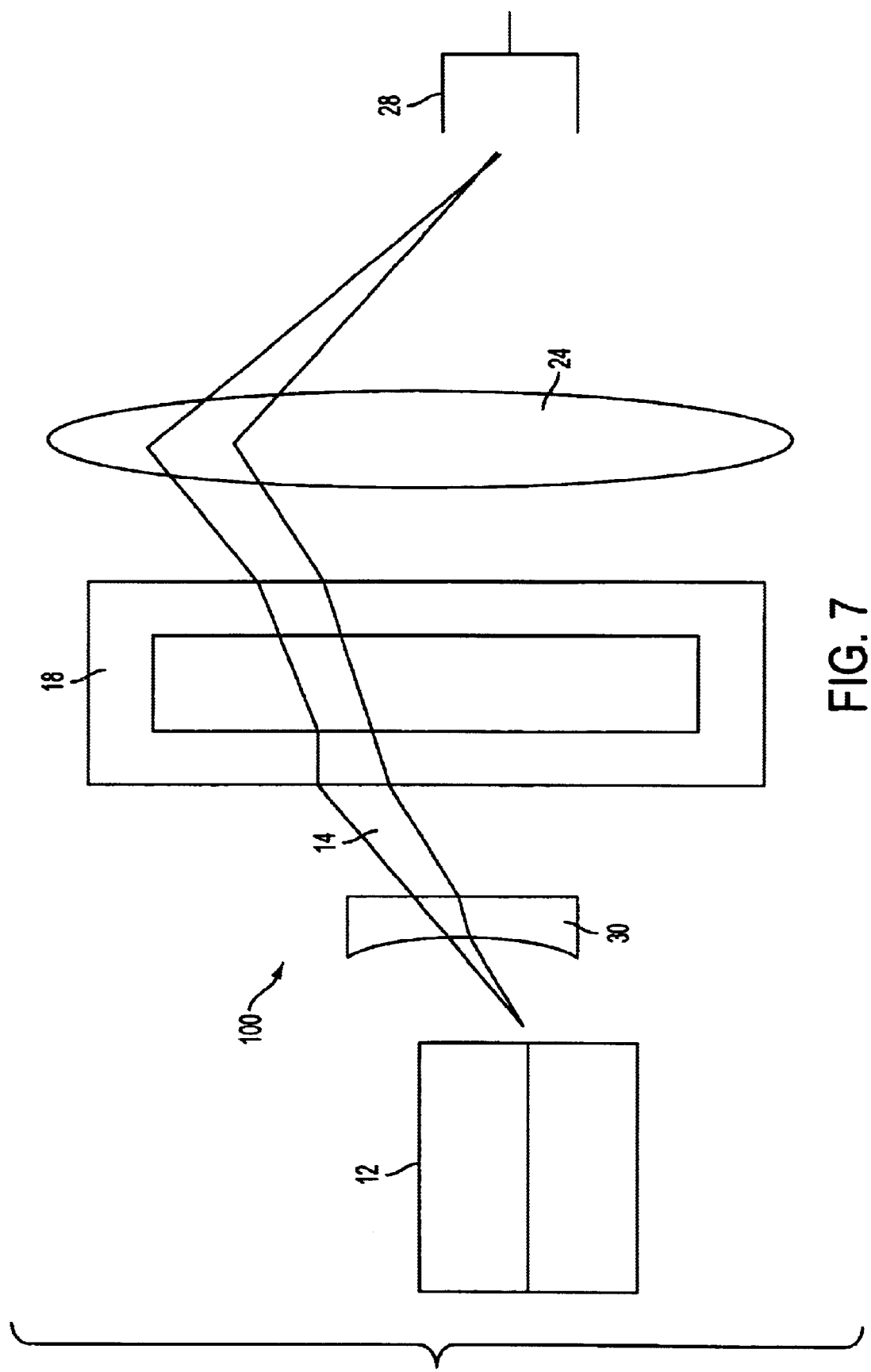

APPARATUS AND METHOD FOR NONDESTRUCTIVE MONITORING OF GASES IN SEALED CONTAINERS

BACKGROUND OF THE INVENTION

1. Field of the Invention

The present invention is related to gas sensing using tunable diode laser absorption spectroscopy, and more particularly, is related to an apparatus and method for nondestructive monitoring of gases in sealed optically transparent containers, using tunable diode laser absorption spectroscopy, while reducing or eliminating etalon interference fringes.

2. Background and Material Information

Tunable diode laser absorption spectroscopy (TDLAS) is a highly selective and versatile technique for measuring many trace atmospheric constituents with detection sensitivities in the sub-parts-per-billion (ppbv) concentration range. Other spectroscopic techniques such as Fourier-transform infrared (FTIR) spectroscopy, which record the interaction of infrared radiation (IR) with experimental samples, measuring the frequencies at which the sample absorbs the radiation and the intensities of the absorptions, do not have as high a sensitivity as TDLAS in the near infrared (NIR) region of the spectrum. Specifically, FTIR spectroscopy can only achieve minimum detectable absorbencies of $10^{-3}$–$10^{-4}$ in a 1 Hz detection bandwidth, whereas TDLAS can achieve $10^{-6}$–$10^{-7}$ in the same detection bandwidth. Thus it is desirable to use TDLAS over FTIR in the NIR spectral region where many atmospherically important constituents have weak molecular overtone and combination absorption bands.

TDLAS utilizes the wavelength response of matter to probe physical and chemical properties. Also, TDLAS determines the concentration of a gas by measuring the amount of light absorbed at a particular wavelength. The intensity of light absorbed is directly related to gas concentration through Beer's law:

$$ln(I_x/I_o)=-n\sigma x$$

where $I_x$ is the intensity of the transmitted light, $I_o$ is the intensity of incident light, n is the concentration gas, $\sigma$ is the absorption cross section, and x is the pathlength.

Applications for laser absorption spectroscopy range from basic chemical kinetics research and environmental monitoring to medical diagnostics and industrial process monitoring. When trace gas concentrations need to be measured, a system must be designed to minimize noise and background signals.

The amplitude of tunable diode laser absorption signals is proportional to the distance, x, (or pathlength) over which a target gas is sampled. Multipass configurations can increase the pathlength, but require the use of collimated laser beams to ensure a laser beam of sufficient power reaches the detection circuitry. In situations where the target gas resides in a sealed optically transparent container, the laser beam must pass through the container walls to sample the target gas. U.S. Pat. No. 5,317,156 which issued to Cooper et al. on May 31, 1994, shows a typical TDLAS system using a multi-pass sample cell.

Most TDLAS systems are limited in sensitivity not by laser or detector noise but by optical fringes superimposed on the measured spectrum. These result from unwanted optical artifacts, or etalons, formed by reflections and scattering in the optical system. FIG. 1 shows a collimated laser beam 11 having a width defined by edges A and B passing through an optically transparent material, such as a glass container wall W. Partial reflected rays, shown as B', occur at the air/container interface. The partial rays B' from one ray are reflected within the wall W and overlap with adjacent incident rays, shown as AB' in FIG. 1, causing interference. These overlapping rays AB' are phase shifted with respect to each other due to the different optical pathlengths traversed and cause constructive interference when the phase shift is 0, and destructive interference when the phase shift is $\pi$. The interference effect from these overlapping laser beams creates the unwanted etalons.

When the interfering beams are incident on a detector (e.g. a photodetector or square law detector) and the laser frequency is scanned, the phase relationship varies, producing a periodic intensity variation in the photo current. The interference pattern in most cases limits the sensitivity of the measurement and obscures small absorption signals. FIG. 2 shows a molecular absorption graph of a TDLAS signal S using a collimator lens. The signal is recovered in a single pass through a sample container and with no signal averaging. The distorting effects of the etalons are evident; the amplitude and frequency of gas absorption feature G is comparable to the amplitude and frequency outside OFQ the gas absorption feature G as a result of interference fringes F, which may obscure the reading, especially when analyzing small concentrations of gas.

The art is replete with devices and techniques that attempt to reduce etalons. These techniques can be categorized as follows; (I) mechanical modulation or dithering of the etalon spacing (ii) modified modulation schemes (iii) background subtraction and (iv) post-detection signal processing.

If the etalon pathlength-difference is mechanically modulated then the fringes will shift relative to the absorption spectrum. As the spectrum is averaged, the fringes will average to zero, provided the modulation amplitude corresponds either to an integral or a large number of fringes. One method of accomplishing this modulation has been demonstrated by Webster, in U.S. Pat. No. 4,684,258, which issued on Aug. 4, 1987. This patent discloses the interposing of an oscillating Brewster plate into the beam at a point between the two surfaces forming the etalon. Oscillating the plate (by typically 1°) varies the optical pathlength through the plate. Because the plate is at the Brewster angle, reflection losses are minimized. One disadvantage of this method that it is difficult to apply to a multi-pass cell without causing significant attenuation of the beam.

U.S. Pat. No. 4,934,816 which issued to Silver et al. On Jun. 19, 1990, discloses a method using a piezoelectric transducer (PZT) to vibrate the mirror or other component which forms one surface of the etalon. However, both the Webster and Silver techniques are difficult to implement when the sample containing the gas to be analyzed is a sealed product container that must be sampled in-situ.

In TDLAS systems using wavelength modulation spectroscopy (WMS), the fringes can be averaged to zero by applying an additional low-frequency wavelength modulation to the diode laser, with an amplitude equal to an integral number of periods of the etalon fringe. As a result, the technique is effective only at removing fringes with a period less than the absorption line width since the modulation amplitude needed to remove longer period fringes would also smear the absorption line shape and reduce its peak height.

For a perfectly stable system a background spectrum, obtained by supplying zero air to the instrument inlet, would display the same etalon fringes as the sample spectrum. Subtraction of this background spectrum would then remove the fringes. Real systems however are subject to thermal drift, so that in the time between taking the sample spectrum and the background spectrum the fringes will have drifted and cancellation will not be perfect. Thus, the success of background subtraction depends firstly on the thermal and mechanical stability of the system and secondly on the rapidity with which sample and background spectra can be alternated.

Post-detection signal processing can take the form either of analog processing of the signal from the look-in amplifier or demodulator, or digital processing of the signal acquired by the signal averager. Both take advantage of the periodic nature of the optical fringes. A simple low-pass filter following the lock-in amplifier can dramatically reduce fine-pitch fringes. In known TDLAS systems, a combination of background subtraction with some form of post-detection processing is most commonly used.

The minimum detectable absorption is given by the smallest variation in $\ln(I_x/I_o)$ that can be distinguished from noise or background signals. Sources of noise include laser intensity fluctuations and detector thermal noise. Many TDLAS techniques exist that overcome these noise sources, such as dual beam cancellation, wavelength modulation and single tone and two tone frequency modulation. In principle, these techniques are capable of achieving shot noise limited detection, which is the fundamental sensitivity limit determined by the statistical nature of converting a photon into an electron at a detector.

In most practical systems using coherent light sources, however, background signals due to optical interference limit detection sensitivities. Optical interference is observed whenever two or more light waves which have traveled different optical pathlengths simultaneously arrive at a detector. For example, in laser absorption spectroscopy, a collimated beam, after passing a transmissive optical element, may be broken up into a number of partial waves which travel along different optical pathlengths before arriving at a detector. As the frequency of the laser is scanned, the relative phases of these partial waves vary, resulting in constructive and destructive interference. The physical manifestation of such interference is a periodic variation in the detected intensity.

When interference-related intensity variations are comparable in amplitude to intensity variations due to gaseous absorption, then measurements of gas concentration become imprecise. Many methods have been developed to reduce the amplitude of interference fringes. However, each method has limitations and such methods are not generally applicable to all situations encountered in laser absorption spectroscopy. Furthermore, the previously-mentioned techniques for reducing etalons are often unreliable and are overly complex, as they use opto-mechanical or electrical techniques which, as described above, are not generally suitable for all situations, particularly when measurements need to be made in-site through sealed product containers. Further, none of the previously-mentioned techniques will reduce interference effects which arise when analyzing the contents of a sealed container.

Many new and existing commercial products have ingredients that are sensitive to atmospheric gases. Prolonged exposure to elevated levels of these gases degrades product quality and potency. Throughout processing, particularly aseptic processing (where sterilization is through filtration), products are held in and transferred between containers where the potential exists for gas exposure. When processing gas-sensitive formulations, ambient levels of reactive gases are reduced with inert gas purges. However, trace quantities of reactive gases can be entrained into solution containers and trapped in the container headspace (i.e., the region above the product and below the seal).

Many known apparatus and methods of gas analysis require the destruction of the container in order to analyze the gas contained therein. Production monitoring of headspace gas is often performed off-line at scheduled intervals. Because this method is slow, the potential for large quantities of off-specification product being produced is significant. One such destructive method is discussed in U.S. Pat. No. 5,900,378, which issued to Mayer et al. on May 4, 1999. Analysis requiring the destruction of the container is not only time-consuming, but is costly for the manufacturer, and is both labor intensive and requires disposal of what may otherwise be perfectly good product. Thus, a fast, sensitive, and nondestructive method and apparatus for monitoring gas concentrations in both on-line and off-line applications are desired.

SUMMARY OF THE INVENTION

The present invention provides a system and method for the nondestructive detection of gas or gas composition in a sealed container. The system of the present invention includes a tunable diode laser source that provides a diverging (i.e., uncollimated) laser beam for absorption in a substance to be analyzed or measured, a detector that detects the laser beam, a zone that accepts one or more of the sealed containers, each container being substantially optically transparent and containing the substance to be measured, the laser source configured to transmit the laser beam through the zone, and a collection lens that focuses the laser beam onto the detector.

The detector of the system may be a square law detector. Also, the collection lens may be convex or biconvex.

The system may further have a diverging lens that diverges the laser beam and that is located between the laser source and the zone. Additionally, the system may include an optical fiber coupled to the source that transmits light to the zone. Also, the collection lens may be stationary.

The invention may further include a reflector, the zone being positioned between the source and the reflector, the laser source configured to transmit the laser beam through the zone and onto the reflector, the reflector returning the laser beam to the collection lens, with the reflector positioned on an opposite side of the zone from the detector, the collection lens and the source.

The method of the present invention includes placing the sealed container in an acceptance zone, providing a diverging laser beam, transmitting the uncollimated laser beam through one wall of the sealed container, transmitting the uncollimated laser beam through another wall of the sealed container, the another wall being opposed to the one wall, focusing the laser beam onto a surface of a detector, and detecting, using a detector, the focused laser beam.

The focusing of the laser beam may include using a collection lens, which may be either convex or biconvex.

The method may further include diverging the uncollimated laser beam before transmitting the uncollimated laser beam through the one wall of the container. The diverging may include using a diverging lens, and the diverging lens may be located between the laser source and the zone.

Additionally, the method may further include transmitting the laser beam through an optical fiber coupled to the source, and transmitting, from the optical fiber, the uncollimated laser beam to the zone. Also, the collection lens may be stationary.

The method may further include collecting the uncollimated laser beam after transmitting the uncollimated laser beam through another wall of the sealed container, reflecting the uncollimated laser beam back through the another wall of the sealed container, and reflecting the uncollimated laser beam back through the one wall of the sealed container.

The present invention is particularly useful for detection of oxygen, moisture and carbon dioxide, and other gases in small volume product containers during pharmaceutical, food and beverage, and consumer electronic production. The present invention can analyze gas samples at online production speeds, can measure trace quantities and can nondestructively analyze gas contents within sealed containers.

When testing small container volumes, a laser beam need not be collimated to ensure sufficient laser power reaches the detector. By allowing the laser beam to diverge at its natural rate, fewer partial rays are incident onto the container at normal incidence. Therefore fewer overlapping rays, having traveled along different optical pathlengths, will be incident on the detector and etalon interference will be minimized. This reduction in background interference improves the signal to background noise ratio and permits trace level gas detection in small diameter containers at relatively high speeds, usually two seconds or less. The diverging beam may be collected using a collection lens such as a biconvex lens, after traversing the container, and focused onto a detector.

BRIEF DESCRIPTION OF THE DRAWINGS

The present invention is further described in the detailed description which follows, in reference to the noted plurality of drawings by way of non-limiting examples of preferred embodiments of the present invention, in which like numerals represent like elements throughout the several views of the drawings, and wherein:

FIG. 7 is a schematic side elevational view of the system for nondestructive detection of gas in a sealed container, according to a second preferred embodiment of the present invention;

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 3:
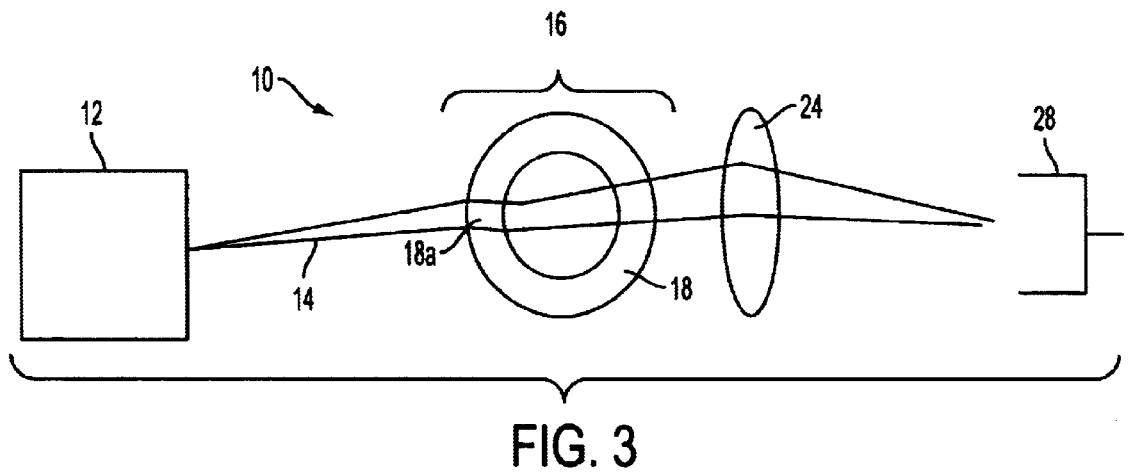
FIG. 3 is a schematic top plan view of the system for nondestructive detection of gas in a sealed container, according to a first preferred embodiment of the present invention.
Figure 4:
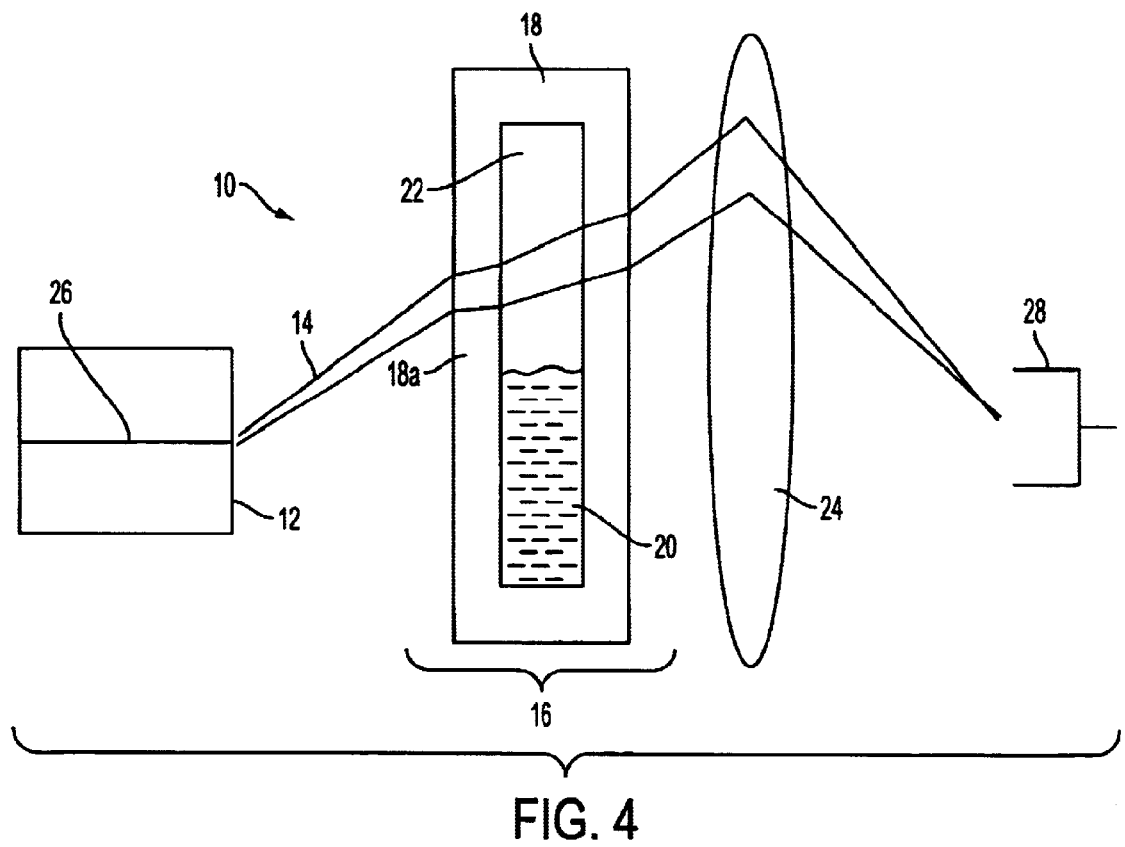
FIG. 4 is a schematic side elevational view of the system for nondestructive detection of gas in a sealed container shown in FIG. 3, according to the first preferred embodiment of the present invention.

Referring to the drawings wherein like numerals represent like elements, FIGS. 3 and 4 show respective schematic plan and side elevational views of the system of an apparatus 10 of a first embodiment of the present invention. The apparatus 10 includes a wavelength-modulated diode laser source 12 for providing a laser beam 14 with an emission frequency corresponding to the absorption frequency of an atom or molecule of a target gas (i.e., a gas to be detected by the apparatus 10 by adjusting the source 12 to generate a laser beam 14 corresponding to the absorption frequency of the target gas).

The apparatus 10 further includes a zone 16 for accepting one or more sealed optically transparent containers 18, constructed of, e.g., glass, plastic or ceramic, that contain a product area 20 which may contain liquid, powderous or solid product, and a headspace area 22, which may contain the target gas. In the preferred embodiment, the container 18 is optically transparent, but in alternative embodiments, the container may be less than completely optically transparent (e.g. translucent).

The laser beam 14 generated by the source 12 is an uncollimated beam (i.e., a diverging beam, or a beam the rays of which have not been rendered parallel), which transmits individual rays through the container 18 at a plurality of angles. The output of the laser source 12 is diffraction limited due to the micron size slit 26 (or p-n junction) through which laser light is emitted. As shown in FIGS. 3 and 4, the laser beam 41 diverges in planes both parallel and perpendicular to the plane of the diode p-n junction 26. The divergence in both directions results in an elliptical far field radiation pattern. Typically, the divergence angle perpendicular to the junction is approximately 2220 and parallel to the junction is approximately 13°.

Figure 1:
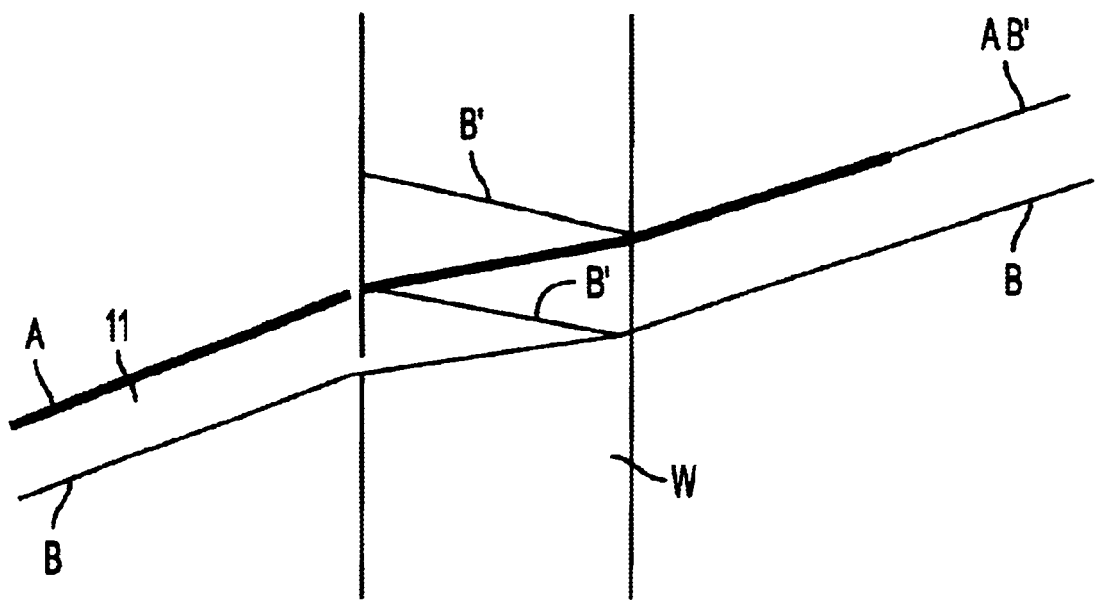
FIG. 1 is a schematic view of a known collimated laser beam passing through an optically transparent material.
Figure 5:
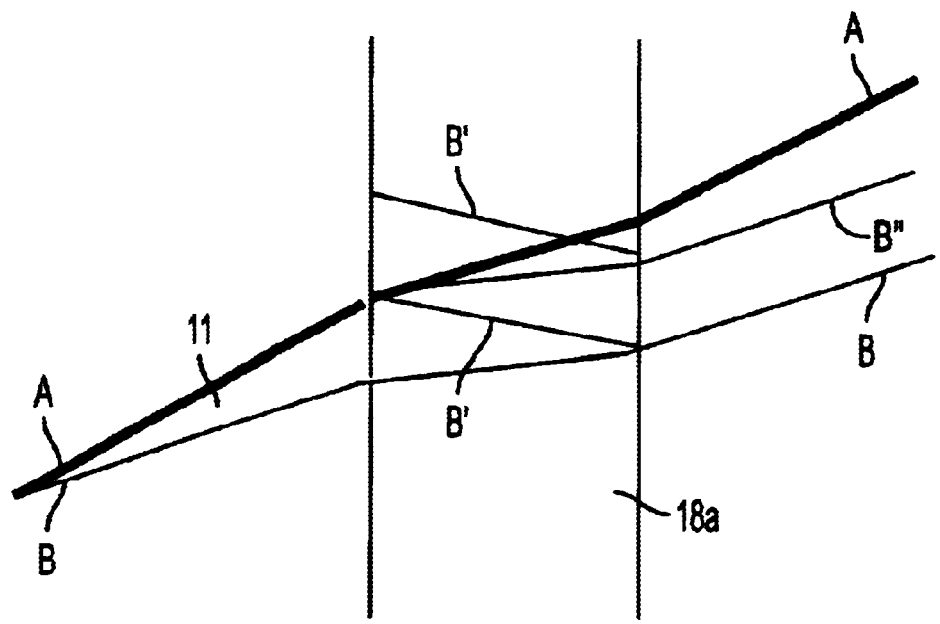
FIG. 5 is a schematic view of a diverging laser beam passing through an optically transparent material, according to the present invention.

FIG. 5 shows an enlarged schematic view of the uncollimated beam 14 passing through one wall 18a of the container 18. Each ray of the beam 14 is incident on the wall 18a at a slightly different angle. Some partial rays B' from the ray B are reflected within the container wall 18a, while other partial rays B" are transmitted through the container wall. Partial ray B" does not overlap incident rays A and B because the partial ray has an angle of incidence different than that of the incident rays A and B. Therefore the incident rays A and B do not interfere with partial rays B' and B", and partial rays to not interfere with incident rays.

Referring again to FIGS. 3 and 4, the apparatus 10 further includes a collection lens 24 and a detector 28. The collection lens 24 focuses the uncollimated (i.e., diverging) beam 14 onto the detector 28. In the preferred embodiment, the collection lens 24 is a biconvex lens, but it is readily appreciable by those skilled in the art that other types of collection lenses may be used in alternative embodiments. Further, in the preferred embodiment, the detector 28 is a square law detector, but it is readily appreciable by those skilled in the art that other types of detectors may be used in alternative embodiments. Thus, the present invention reduces the number of overlapping rays which reach the detector 28, since each ray is incident on the container at a slightly different angle.

The present embodiment passes the laser beam 14 from the source 12 to the detector 28 at a single time. For certain industrial applications (e.g., analyzing gas content of small volume glass containers 18, having e.g., volumes ranging from approximately 1 ml to approximately 100 ml), a single pass configuration provides sufficient sensitivity to make accurate measurements. When testing containers 18 having such small volumes, a laser beam 14 need not be collimated to ensure sufficient laser power reaches the detector 28. By allowing the laser beam 14 to diverge at its natural rate, fewer partial rays are incident onto the container 18 walls at normal incidence. Therefore fewer overlapping rays, having traveled different optical pathlengths, will be incident on the detector 28 and etalon interference will be minimized.

The operation of the apparatus of the present invention will now be described. The source 12 provides a diverging laser beam 14, which passes one time through a container 18 which may contain the target gas. The transmitted light of the diverging beam 14 is then collected by a collection lens 24 and focused onto the detector 28. The lens 24 may be adjusted to increase the versatility of the apparatus 10, e.g., to accommodate containers 18 of various size. However, during operation of the apparatus 10 (i.e., during gas monitoring), the lens 24 is stationary.

Figure 6:
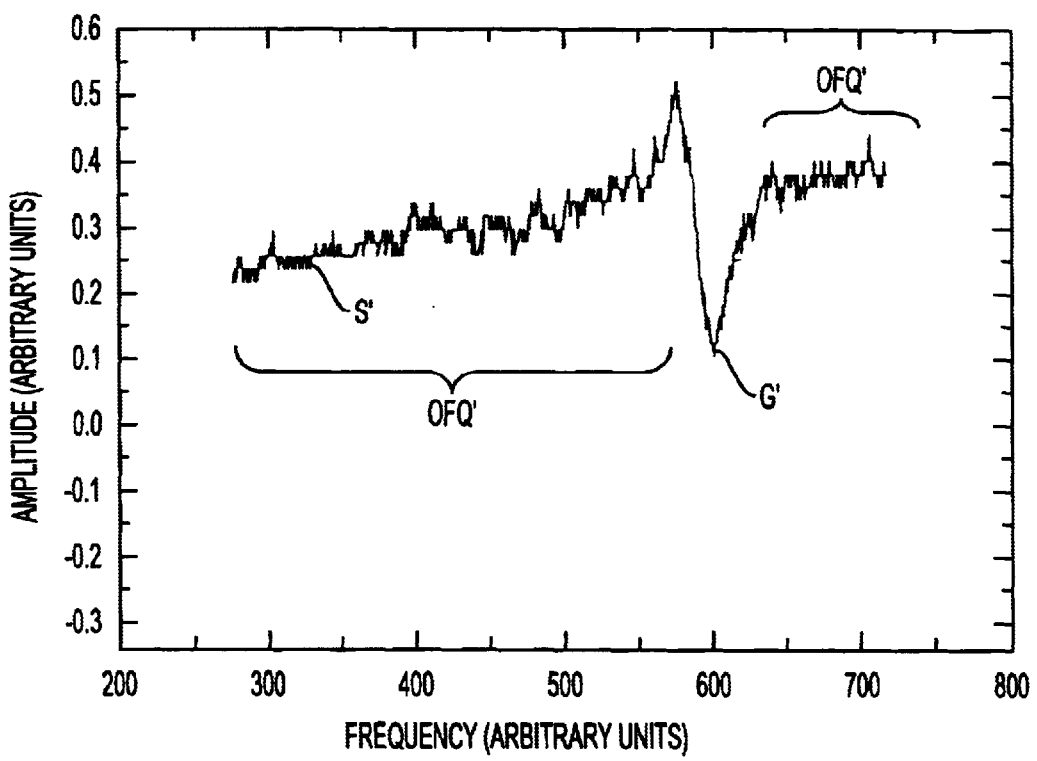
FIG. 6 is a molecular absorption graph of a TDLAS signal using a diverging laser beam of the present invention.
Figure 2:
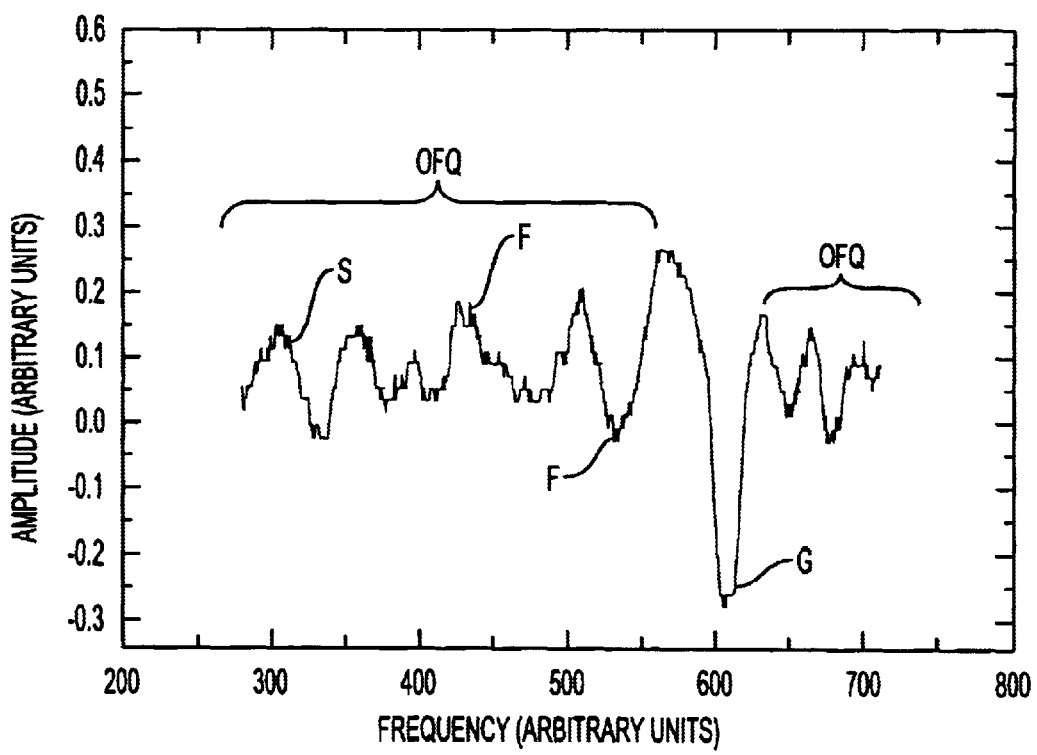
FIG. 2 is a molecular absorption graph of a TDLAS signal using a known collimator lens.

FIG. 6 shows a molecular absorption graph of a TDLAS signal S' using a diverging laser beam of the present invention. The signal is recovered in a single pass through the container 18 and with no signal averaging. The amplitude of gas absorption feature G' is easily distinguished from those outside the frequency OFQ' of the gas absorption feature. Thus, detecting and analyzing small volumes of gas is easily performed.

FIG. 7 shows an apparatus 100 according to a second preferred embodiment of the present invention. The configuration of the second embodiment is similar to that of the first embodiment, but includes a diverging lens 30 to control the amount of divergence of the laser beam.

Figure 8:
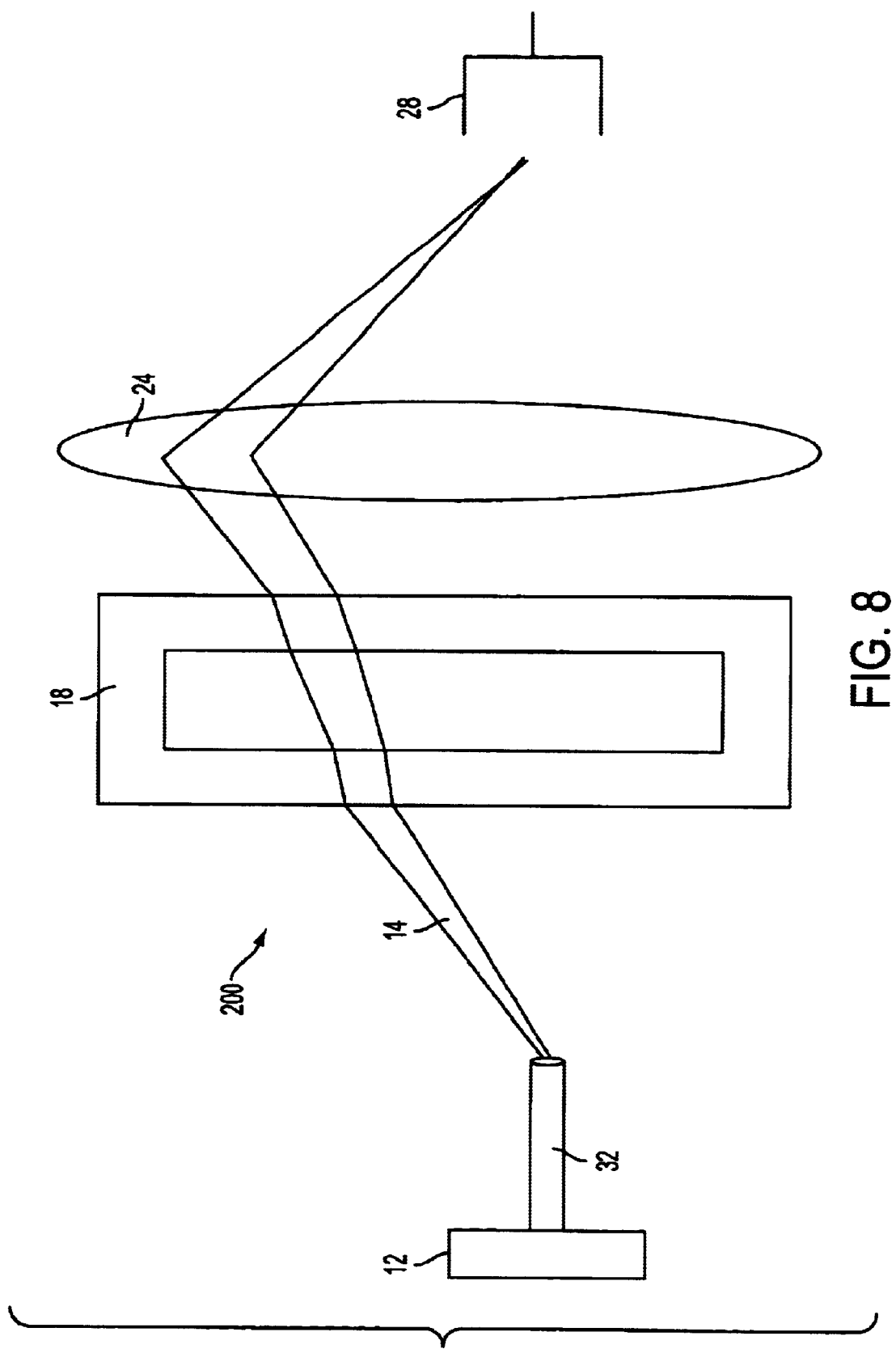
FIG. 8 is a schematic side elevational view of the system for nondestructive detection of gas in a sealed container, according to a third preferred embodiment of the present invention.

FIG. 8 shows an apparatus 200 according to a third preferred embodiment of the present invention. The configuration of the third embodiment is similar to that of the first embodiment, but includes an optical fiber 32 affixed to the source 12 for delivering the beam 14 to the container 18 and onto the sensor 28. The output of the fiber 32 also diverges due to the small diameter of the fiber core. This embodiment enables flexibility of the design of the apparatus 10.

Figure 9:
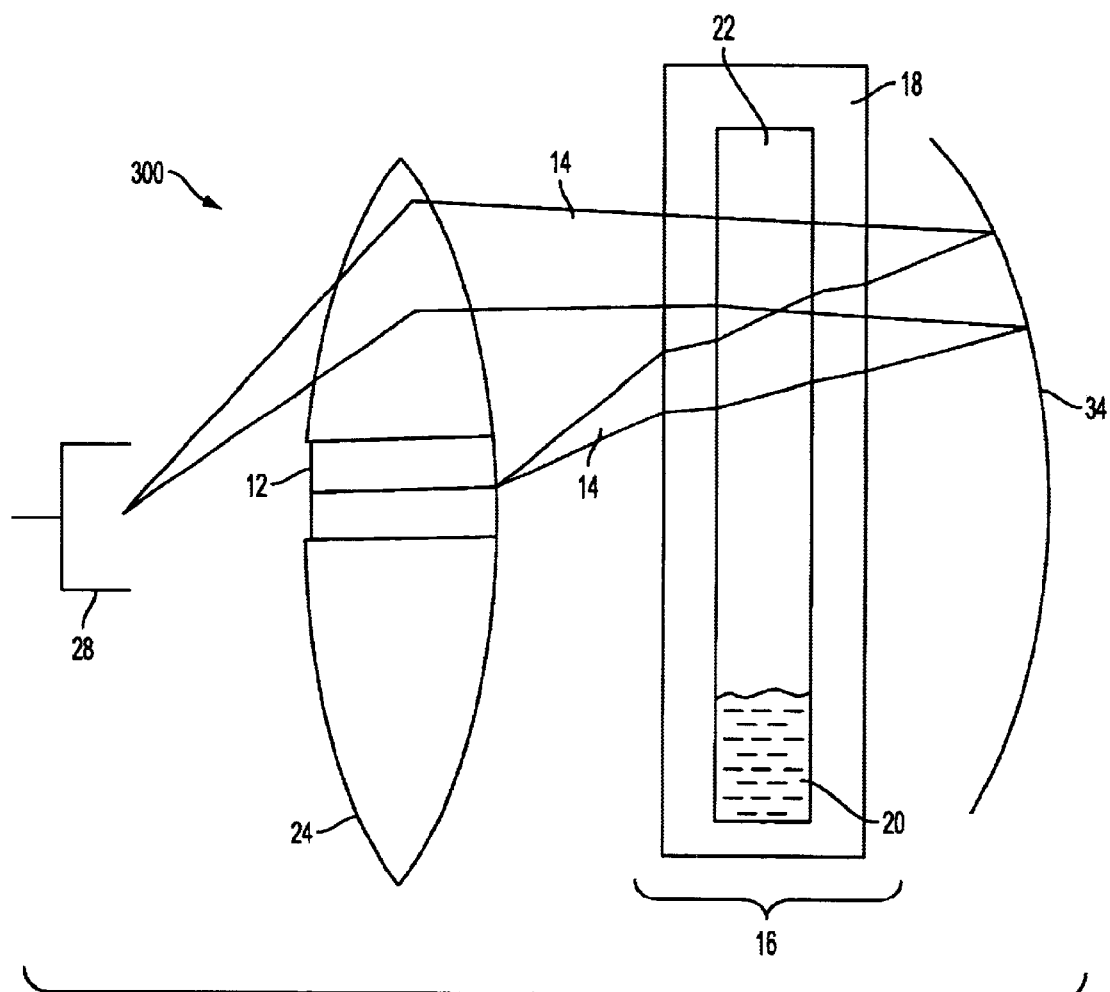
FIG. 9 is a schematic side elevational view of the system for nondestructive detection of gas in a sealed container, according to a fourth preferred embodiment of the present invention.

FIG. 9 shows an apparatus 300 according to a fourth preferred embodiment of the present invention. The configuration of the fourth embodiment is similar to that of the first embodiment, but includes a reflector 34 for collecting the beam 14 after it has passed through the container 18. The reflector 34 of the fourth embodiment may be a flat mirror, a parabolic mirror or a retroreflector. Once collected, the beam is reflected and again passed through the container 18, where it is collected through the collection lens 24 and focused onto the detector 28. In the dual-pass configuration of the fourth embodiment, the pathlength is increased by a factor of two. Further, the interference amplitude does not increase since there is no overlap of the beam 14.

The present invention improves the sensitivity of laser absorption measurements by implementing a diverging laser beam 14. In a single or double pass configuration, the optical arrangement has a minimum number of optical components which reduces the potential for etalon interference fringes and allows for a compactness and cost savings. The compact nature of the invention also reduces the pathlength outside the container 18 which in turn reduces the amount of background gas that needs to be purged from the system. Also, the features of any of the above-described embodiments may be used in any combination. For example, the optical fiber 32 of the third embodiment may be used in combination with the reflector 34 of the fourth embodiment.

It is noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for nondestructive detection of gas in a sealed container, the system comprising:
   a tunable diode laser source that provides a diverging laser beam for absorption in a substance to be measured;
   a detector that detects the laser beam;
   a zone that accepts one or more of the sealed containers, each container being substantially optically transparent and containing the substance to be measured, said zone located between said detector and said laser source, said laser source configured to transmit the laser beam through said zone; and
   a collection lens that focuses said laser beam onto said detector, said lens located between said zone and said detector.

2. The system according to claim 1, wherein said detector is a square law detector.

3. The system according to claim 1, wherein at least one surface of said collection lens is convex.

4. The system according to claim 1, further comprising a diverging lens that increases the divergence of the diverging laser beam, said diverging lens located between said laser source and said zone.

5. The system according to claim 1, further comprising an optical fiber coupled to said source that transmits light to said zone.

6. The system according to claim 1, wherein said collection lens is stationary.

7. A system for nondestructive detection of gas in a sealed container, the system comprising:
   a tunable diode laser source that provides a diverging laser beam for absorption in a substance to be measured;
   a zone that accepts one or more of the sealed containers, each container being substantially optically transparent and containing the substance to be measured;
   a detector that detects said laser beam;
   a collection lens that focuses said laser beam onto said detector, said lens located between said zone and said detector,
   a reflector, said zone positioned between said source and said reflector, said laser source configured to transmit the laser beam through said zone and onto said reflector, said reflector returning the laser beam to said collection lens, said reflector positioned on an opposite side of said zone from said detector, said collection lens and said source.

8. The system according to claim 7, wherein said detector is a square law detector.

9. The system according to claim 7, wherein at least one surface of said collection lens is convex.

10. The system according to claim 7, further comprising a diverging lens that increases the divergence of the diverging laser beam, said diverging lens located between said laser source and said zone.

11. The system according to claim 7, further comprising an optical fiber coupled to said source that transmits light to said zone.

12. The system according to claim 7, wherein said collection lens is stationary.

13. The system according to claim 7, wherein said reflector is one of a flat mirror, a parabolic mirror and a retroreflector.

14. A method for nondestructive detection of gas in one or more sealed, substantially optically transparent, containers, the method comprising:

provided an acceptance zone adapted to receive the one or more containers;

providing a diverging laser beam;

transmitting the laser beam through opposed first and second walls of the container positioned in the zone;

focusing the laser beam onto a surface of a detector; and detecting, using a detector, the focused laser beam.

15. The method according to claim 14, wherein the detector is a square law detector.

16. The method according to claim 14, wherein said focusing comprises using a collection lens.

17. The method according to claim 16, wherein at least one surface of the collection lens is convex.

18. The method according to claim 16, wherein the collection lens is stationary.

19. The method according to claim 14, further comprising increasing the divergence of the diverging laser beam before said transmitting the laser beam through the opposed first and second walls of the container.

20. The method according to claim 19, wherein said increasing the divergence comprises using a diverging lens.

21. The method according to claim 20, wherein said diverging lens is located between the laser source and the zone.

22. The method according to claim 14, further comprising:

transmitting the laser beam through an optical fiber coupled to the source; and transmitting, from the optical fiber, the laser beam to the zone.

23. The method according to claim 14, further comprising:

collecting the laser beam after said transmitting of the laser beam through the opposed first and second walls of the container;

reflecting the laser beam back through the second wall of the sealed container; and transmitting the laser beam back through the first wall of the sealed container;

wherein said focusing of the laser beam onto a surface of a detector is after said transmitting of the laser beam back through the first wall of the sealed container.

* * * * *